United States Patent
Erndt et al.

(10) Patent No.: US 10,424,857 B2
(45) Date of Patent: Sep. 24, 2019

(54) CONNECTOR DEVICE WITH CONNECTOR AND ASSEMBLY METHOD

(71) Applicant: Braun GmbH, Kronberg (DE)

(72) Inventors: Andreas Erndt, Kelkheim (DE); Michael Steghaus, Frankfurt am Main (DE); Jan Christian Langsdorf, Oberursel (DE); Torsten Klemm, Eschborn (DE)

(73) Assignee: Braun GMBH, Kronberg (DE)

( * ) Notice: Subject to any disclaimer, the term of this patent is extended or adjusted under 35 U.S.C. 154(b) by 0 days.

(21) Appl. No.: 15/949,433

(22) Filed: Apr. 10, 2018

(65) Prior Publication Data
US 2018/0309218 A1    Oct. 25, 2018

(30) Foreign Application Priority Data

Apr. 21, 2017  (EP) .................................... 17167531

(51) Int. Cl.
*H01R 4/26*     (2006.01)
*H01R 13/11*    (2006.01)
(Continued)

(52) U.S. Cl.
CPC ............ *H01R 13/112* (2013.01); *A61C 17/16* (2013.01); *H01R 4/245* (2013.01); *H01R 4/48* (2013.01); *H01R 12/585* (2013.01); *H01R 12/7076* (2013.01); *H01R 13/055* (2013.01); *H01R 13/432* (2013.01); *H01R 12/7023* (2013.01); *H01R 12/7029* (2013.01);
(Continued)

(58) Field of Classification Search
CPC .. H01R 13/112; H01R 4/245; H01R 12/7076; H01R 4/48; H01R 13/432; H01R 13/055; H01R 43/16

USPC .................. 439/775, 862, 82, 751, 943, 500
See application file for complete search history.

(56) References Cited

U.S. PATENT DOCUMENTS 5,257,947 A    11/1993  Scheer et al.
5,431,576 A *   7/1995  Matthews ............ H01R 13/113
                                                   439/247
(Continued)

FOREIGN PATENT DOCUMENTS

WO      WO 9315532         8/1993
WO      WO 2018011195 A1 *  1/2018

OTHER PUBLICATIONS

European search report dated Oct. 11, 2017.

*Primary Examiner* — Abdullah A Riyami
*Assistant Examiner* — Nelson R. Burgos-Guntin
(74) *Attorney, Agent, or Firm* — Ronald T. Sia; Kevin C. Johnson

(57) ABSTRACT

A connector is disclosed comprising at least one contact clip. The contact clip comprises an electrically conductive substrate having a longitudinal axis, a first terminal located at a first end of the substrate, wherein the first terminal comprises at least two contact tongues between which a longitudinal slot is formed, which contact tongues are elastically deformable with respect to each other in a first direction which is perpendicular to the longitudinal axis, and a second terminal located at a second end of the substrate. The connector may further comprise a chassis and a PCB. In addition, a device comprising an energy consumer, an electrical energy source, a PCB and at least one connector is disclosed.

17 Claims, 4 Drawing Sheets

(51) Int. Cl.
*H01R 4/245* (2018.01)
*H01R 4/48* (2006.01)
*H01R 12/70* (2011.01)
*H01R 13/05* (2006.01)
*H01R 13/432* (2006.01)
*A61C 17/16* (2006.01)
*H01R 12/58* (2011.01)
*H01R 43/16* (2006.01)
*H01R 12/71* (2011.01)
*H01R 13/20* (2006.01)
*H01R 13/24* (2006.01)
*H01R 13/26* (2006.01)

(52) U.S. Cl.
CPC .......... *H01R 12/714* (2013.01); *H01R 13/052* (2013.01); *H01R 13/20* (2013.01); *H01R 13/2442* (2013.01); *H01R 13/26* (2013.01); *H01R 43/16* (2013.01)

(56) References Cited

U.S. PATENT DOCUMENTS

| | | | | |
|---|---|---|---|---|
| 5,575,690 A * | 11/1996 | Eaton | ................... | H01R 13/187 439/176 |
| 5,630,720 A * | 5/1997 | Kocher | ................. | H01R 13/642 439/678 |
| 6,210,240 B1 * | 4/2001 | Comerci | ............ | H01R 12/7088 439/853 |
| 6,299,492 B1 * | 10/2001 | Pierini | ................... | H01R 13/26 439/884 |
| 6,835,103 B2 * | 12/2004 | Middlehurst | ........ | H01R 13/113 439/699.1 |
| 6,974,329 B2 * | 12/2005 | Henneberg | ........... | H01R 12/585 439/59 |
| 7,104,812 B1 * | 9/2006 | Bogiel | ................... | H01R 13/03 439/79 |
| 7,112,071 B2 * | 9/2006 | Nakagawa | ........... | H01R 13/112 439/82 |
| 7,641,500 B2 * | 1/2010 | Stoner | ................. | H01R 13/633 439/357 |
| 7,997,936 B2 * | 8/2011 | Yu | ........................ | H01R 13/055 439/190 |
| 8,968,010 B2 * | 3/2015 | Endo | ........................ | H01R 4/48 439/82 |
| 9,257,778 B2 * | 2/2016 | Buck | .................... | H01R 13/516 |
| 2009/0209143 A1 * | 8/2009 | Wu | ....................... | H01R 13/055 439/862 |

\* cited by examiner

Figure 1
Figure 2
Figure 3
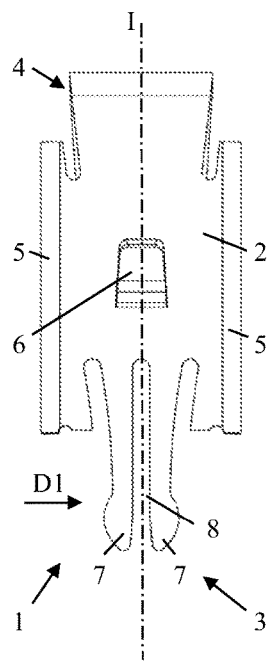
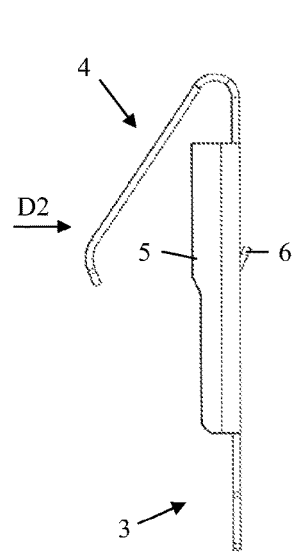
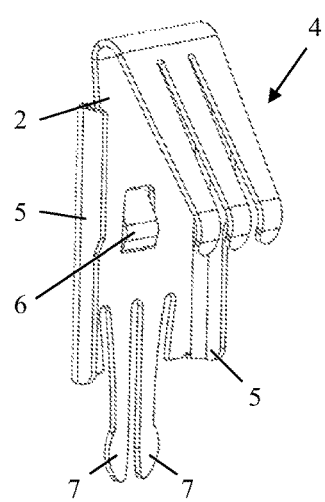
Figure 4
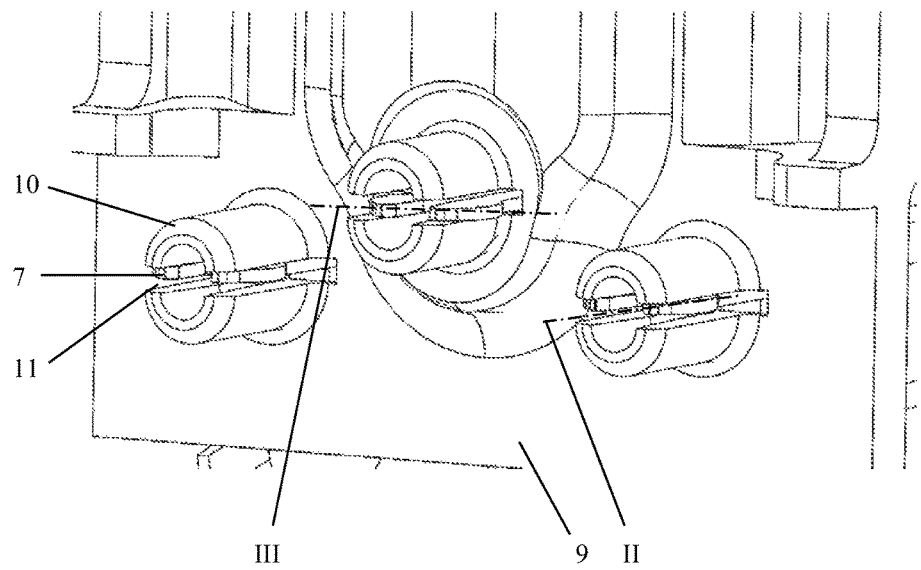

CONNECTOR DEVICE WITH CONNECTOR AND ASSEMBLY METHOD

FIELD OF THE INVENTION

The invention relates to a connector and a device comprising such a connector. The device may be a household device or a body treatment device, for example an electric toothbrush, an electric shaver, an electric epilator or the like. The connector may comprise at least one contact clip having an electrically conductive substrate with a longitudinal axis, a first terminal located at the first end of the substrate and a second terminal located at a second end of the substrate. The connector may further comprise a chassis and/or a PCB (printed circuit board). Further, the invention relates to a method for assembling a device comprising a connector.

BACKGROUND OF THE INVENTION

There are many different options to connect electromechanical components on a PCB. A very common and broadly used version is to connect via electrical wires, which can be soldered to the PCB and the battery. This is the typical solution for a manual assembly in manufacturing. There are further solutions to enable the electrical connection via automated assembly. However, the effort (machinery, specific designed equipment) needed to integrate the assembly into an automated production is high.

In US 2005/0019654 A1 a battery is disclosed having two contact terminals which are attached to the battery by welding. Each of the terminals comprises a fixing portion designed for fixing the battery via the terminals to a PCB without soldering.

Further, WO 2010/130655 A1 discloses a mechanical and electrical connection of PCBs by means of connection elements having terminals at opposite ends. Each of the terminals comprises two contact tongues between which a longitudinal slot is formed. The longitudinal slot is open toward the respective free end of the contact element. The outwardly directed outer edge of the contact tongues is slightly convex, as is the inner edge of the contact tongues which is directed toward the slot.

SUMMARY OF THE INVENTION

It is accordingly one object of the present invention to provide an improved connector suitable for different types of devices with the connector providing a reliable electrical connection to the PCB while reducing the effort for mounting the PCB and the connector.

This object is solved by a connector according to claim 1 and a device according to claim 15.

According to the first aspect, the connector comprises at least one contact clip. The contact clip preferably comprises an electrically conductive substrate having a longitudinal axis, a first terminal located at the first end of the substrate and a second terminal located at a second end of the substrate. The first terminal may comprise at least two contact tongues between which a longitudinal slot is formed, which contact tongues are elastically deformable with respect to each other in the first direction which is perpendicular to the longitudinal axis. In its unstressed condition, the second terminal may be bent with respect to the substrate and/or the first terminal. Further, the first terminal may be elastically deformable with respect to the substrate in a second direction which is perpendicular to the first direction and perpendicular to the longitudinal axis.

The invention proposes a beneficial way to connect an electronic component part, like a battery or a DC-motor, with a PCB which is suitable for an automated assembly of the e.g. battery to the PCB. The design of the contact clip of the connector increases the reliability of the manufacturing process due to a simplified assembly operation of the battery and/or the battery holder to the PCB. The assembly of the electromechanical components onto the PCB becomes a pure mechanical standard-like assembly process without the need to combine typical PCB-handling operations (like soldering) with typical mechanical assembly operations (defined movements, normally done via robots). In addition, the design results in reduced costs due to less parts and due to avoidance of soldering or other additional steps which are typically used to ensure a reliable and low-resistance electrical connection (simplified production process, lower production asset cost). Further, the contact clip provides a detachable connection, which is an advantage in maintenance and repair of the device but also in manufacturing, where pre-assembled units can be separated and at least partially reused in case of detection of a malfunction in a later production step (reversible assembly).

According to a second independent aspect, a connector comprises a chassis adapted for receiving at least one contact clip. The chassis may comprise a first area adapted for attachment of a PCB and a second area adapted for attachment of at least one electronic component. The first area preferably comprises at least one slotted male plug. The slotted male plug may be adapted to receive a first terminal of a contact clip. For example, a connector comprises a chassis or battery holder with several slotted male plugs which are each adapted to receive a respective contact clip, wherein the slotted male plugs may be assigned to portions of the chassis or battery holder or may be assigned to compartments for receiving one or more electronic components, like an energy source, a motor or the like.

Further aspects are mentioned in the further claims and explained in the following detailed description of example embodiments according to the proposal. It is to be noted that these aspects are explained with reference to certain embodiments of the proposal. These embodiments might realize one or more of the different preferred features of the proposal. The different aspects or features of the proposal with the related advantages and effects as described and/or evident for the one skilled might be combined without departing from the present invention in any useful combination. The one skilled in the art will acknowledge that any combination of the different aspects or features of the following disclosure in the description and/or the drawings is useful for specific aspects of the proposal, even without combination with other aspects or features disclosed together in one embodiment.

BRIEF DESCRIPTION OF THE DRAWINGS

FIG. 1 shows a top view of a contact clip according to a first embodiment.

FIG. 2 shows a side view of the contact clip of FIG. 1.

FIG. 3 shows a perspective view of the contact clip of FIG. 1.

FIG. 4 shows a perspective view of a detail of the chassis according to an embodiment receiving the contact clip of FIG. 1.

DETAILED DESCRIPTION OF THE INVENTION

Figure 5:
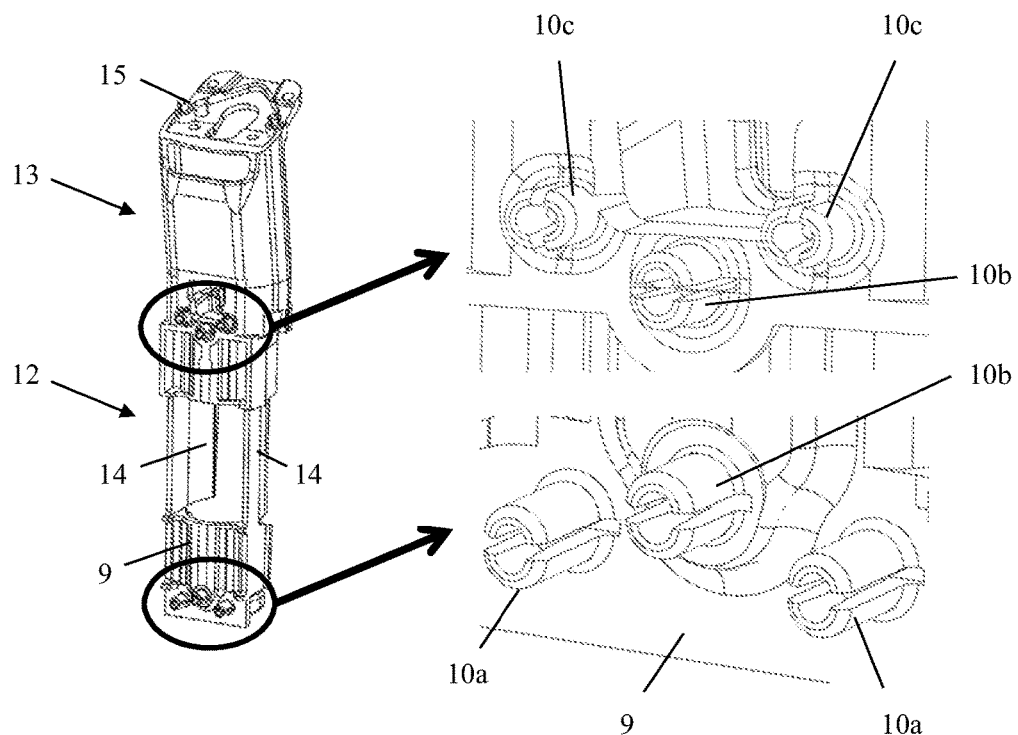
FIG. 5 shows a perspective view of the chassis of FIG. 4 with enlarged details.

The invention is disclosed in the following by way of exemplary embodiments realizing different features and aspects of the invention.

The contact clip of the connector may be designed such that the substrate and the first terminal extend at least substantially in a common plane along the longitudinal axis. As an alternative, the first terminal may be arranged in a bent configuration with respect to the substrate. The first terminal may be designed such that the longitudinal slot, in its unstressed condition, has a constant width and is open toward the respective free end of the first terminal. The outwardly directed outer edge of the contact tongues may be slightly convex. As an alternative, the outwardly directed outer edge of the contact tongues may comprise a section having an increased width.

The second terminal may be formed by folding a portion of the substrate onto the remaining portion of the substrate such that the second terminal and the remaining portion of the substrate form reflex angle. As an alternative, the second terminal and the remaining portion of the substrate may form an obtuse angle. The second terminal may comprise two or more tongues with longitudinal slots extending there between.

The contact clip of the connector may further comprise at least one elastically deformable lug. Preferably, in its unstressed condition, this lug is bent with respect to the substrate. For example, the lug may form an acute angle with the substrate. The lug may exert a clamping force on a battery holder or a chassis, thereby contributing in fixing the contact clip. In addition, or as an alternative, the lug may prevent that the contact clip is withdrawn from a battery holder or a chassis, thereby again contributing in fixing the contact clip.

The contact clip of the connector may further comprise at least one lateral guiding rib extending perpendicular to the substrate. The guiding rib may align the contact clip in a battery holder or a chassis. In addition, or as an alternative, the guiding rib may contribute in increasing stiffness of the contact clip in the area of the substrate. This may be beneficial during mounting of the contact clip.

According to a preferred embodiment, the substrate, the first terminal and the second terminal of the contact clip are a single-piece component part. The mechanical connection by means of the contact clip half of the advantage of a mono-fraction disposal compared with a mix of different materials when soldering components to the PCB. The contact clip may consist of or comprise an electrically conductive material, like copper or a copper alloy. For example, the contact clip may consist of CuNi3Si1Mg.

The contact clip preferably has a thickness of the contact tongues and/or the substrate between 0.1 mm and 0.35 mm, preferably about 0.25 mm. Depending on the material of the contact clip, this permits flexibility of the contact clip in the area between the substrate and the second terminal. Further, the contact clip has sufficient rigidity to be mounted in an automated process.

According to a second aspect, the connector further comprises a chassis (or battery holder) receiving at least one contact clip. The chassis comprises a first area adapted for attachment of a PCB and a second area adapted for attachment of at least one electronic component, like an electric motor, an, e.g. rechargeable, battery or the like. The first area comprises at least one slotted male plug adapted to receive the tongues of the first terminal of the at least one contact clip in the slot of the at least one male plug. In other words, the invention proposes that the electrical contacts (e.g. metal sheet) are embedded into a chassis or battery holder in a way, that a portion of the chassis or battery holder is providing the male plug housing, and the PCB has openings providing the respective female plugs (receptors).

Preferably, the electrical contact clips are shaped to an oversized dimension with respect to the PCB-opening, so that the required contact pressure between the male-plug (electrical contact) and the female plug (openings in the PCB) is generated during assembly of the chassis or battery holder and the PCB. The tongues of the contact clips are preferably flexible as mentioned above to adapt to the (smaller) PCB-openings and still keep a pre-stressing to enable an electrically safe, low resistance, functional and reliable connection.

The male plugs provided by the chassis may be round shaped. In more detail, the male plug has the form of a slotted cylinder or a slotted round pipe, wherein the slot formed in the male plug extends in a plane defined by a central longitudinal axis of the male plug and an axis perpendicular to the central longitudinal axis. In other words, the slot divides the male plug e.g. into two half cylinders. The around shape is advantageous because the orientation of the chassis or battery holder towards the PCB is typically defined by several male plugs and therefore the round shape provides a degree of freedom to avoid that the chassis or battery holder is over-determined relative to the PCB.

The slotted male plugs may have a design facilitating insertion into a plated-through opening of the PCB. For example, a slotted male plug may comprise a bezel or chamfer at the free end of the slotted male plug. In addition, or as an alternative, a slotted male plug may be slightly conical with the smaller diameter at the free end of the slotted male plug.

To secure of the contact clip in the slot formed in the male plug, the slot may have a width which is equal to or larger than the thickness of the first terminal of the at least one contact clip. Preferably, the width of the slot is slightly larger than the thickness of the first terminal to allow smooth insertion of the first terminal into the male plug. On the other hand, the width of the slot has to be small enough to prevent undesired deformation of the first terminal in a direction perpendicular to the plane defining the slot.

The chassis may further comprise a guiding section receiving the substrate and/or the at least one lateral guiding rib of the connection clip. The guiding section may comprise a flat wall portion against which the lug of the contact clip abuts. A difference to known connectors is that the male plugs are not snap-fitted to the PCB. Known connectors typically provide a snap-fit connection once the parts are assembled. The connector according to the present invention preferably does not have a snap fit but provides a detachable connection between the PCB and the chassis and/or the contact clip. Providing a snap fit not only adds complexity to the design of the connector but also prevents detachment of the PCB without damaging component parts. Instead of a snap fit, the connector may be encased (wrapped) by other parts of a subassembly of the device, for example component parts housing the PCB, the battery-holder and/or the battery.

Positioning of the PCB may be facilitated if the first area further comprises at least one positioning pin extending parallel to the at least one slotted male plug.

According to a preferred embodiment of the connector, the second area comprises a compartment for receiving an electric motor and/or a compartment for receiving an energy storage or energy source. The compartment for receiving the electric motor four may comprise a mounting wall for attaching the motor. The compartment for receiving the energy storage or energy source may comprise elastically deformable clamping walls for fixing energy storage or energy source.

For example the first area comprises six slotted male plugs, each receiving the first terminal of a respective contact clip, the second area comprises a first compartment for receiving an electric motor, with the second terminals of two contact clips extending in the first compartment, and the second area comprises a second compartment for receiving an energy storage, with the second terminals of two contact clips extending in the second compartment, wherein the second terminals of two further contact clips are positioned at a lateral side of the chassis.

As mentioned above, it is preferred if a PCB is releasably attached to the first area of the chassis. The PCB may comprise at least one plated-through opening receiving a slotted male plug of the chassis and the contact tongues of the first terminal of a contact clip. Preferably, the plated-through opening has a diameter in the direction of the slot of the male plug which is smaller than the maximum width of the first terminal received in the respective plated-through opening and/or the plated-through opening has a diameter in the direction perpendicular to the slot of the male plug which is smaller than the maximum width of the male plug received in the respective plated-through opening.

According to a further aspect, a device comprising an energy consumer, an electrical energy source, a PCB and at least one connector as defined above is provided. The device may be a household device or a body treatment device, for example an electric toothbrush, an electric shaver, an electric epilator or the like.

Compared with known connectors in such devices with electrical conductive part-to-PCB-connections the proposed design of the connector does not require specific assembly and handling operations, is less error-prone and is reversible with less effort. During manufacturing a simplified assembly method may be applied based on the proposed simplified connection of the battery-contact to the PCB. A method according to the present disclosure may comprise, irrespective of the above mentioned features, the following steps: The contact clips are assembled to the chassis or battery holder; the chassis or battery-holder with the contact clips and the energy storage (e.g. battery) is assembled to the PCB; the electrical connection between the contact clips and the PCB comes automatically via the assembly process. Thus, there are no separate action steps required.

An important aspect of the present disclosure is the combination of the chassis or battery holder with a specific designed connection clip. Both parts together form a male plug of the connector, which delivers an electrical connection after being assemble to the respective female plug in the PCB. The female plug in the PCB is a hole using the so called via in the double sided PCB to get the electrical connection to the male contact.

A further important aspect of the present disclosure is an assembly method for a connector comprising the steps of: providing a chassis, at least one contact clip and a PCB; then preassembling the chassis and the at least one contact clip by inserting a first terminal of the at least one contact clip into a slot of at least one male plug of the chassis such that the at least two contact tongues of the first terminal laterally protrude from the at least one male plug in a first direction; then releasably attaching the PCB on a first area of the chassis by inserting at least one slotted male plug into a plated-through opening of the PCB, wherein an elastic clamping force is generated between the PCB and the at least one contact clip by elastic deformation of the at least two contact tongues of the first terminal in the first direction. Optionally at least one electronic component may then be attached to the chassis.

In other words, the PCB is releasably fixed on the chassis by means of the elastic clamping force between the contact clip and the PCB which is caused by elastic deformation of the contact tongues of the contact clip when being inserted into the plated-through opening of the PCB. An additional clamping force between the slotted male plug of the chassis and the plated-through opening of the PCB is not required, but may occur depending on the tolerances between the slotted male plug of the chassis and the plated-through opening of the PCB. This assembly method provides a reliable electrical connection between the contact clip and the PCB and is additionally suitable for releasable attachment of the PCB on the chassis. The latter aspect is especially helpful if a PCB is to be replaced, e.g. during quality control or repair.

In addition to the above mentioned elastic clamping force exerted by interaction of the contact tongues of the first terminal in the plated-through opening of the PCB, the releasable attachment may be supported by a form-locking engagement of an, e.g. cylindrical, positioning pin in a positioning hole of the PCB. Such an additional clamping between the PCB and the chassis does not prevent or hinder nondestructive removal of the PCB from the chassis.

With respect to FIGS. 1 to 3, a first embodiment of a contact clip 1 of a connector is depicted in an unstressed condition, i.e. without forces acting on the contact clip 1. The contact clip 1 comprises a substrate 2 made of an electrically conductive material, for example comprising copper. As shown in FIG. 1, the substrate 2 forms a middle portion of the contact clip 1, while the first terminal 3 and a second terminal 4 extend from opposite ends of the substrate. Further, the substrate 2 comprises lateral guiding ribs 5 provided on both sides of the substrate 2 in the depicted embodiment. The substrate 2 further comprises a lug 6 which is bent with respect to the plane of the substrate 2. The lug 6 is connected to the substrate 2 at one edge and separated from the substrate 2 at three edges. Due to the inclination of the lug 6 with respect to the plane of the substrate 2, one edge of the lug 6 protrudes from the substrate 2 as shown in FIG. 2. A longitudinal axis I of the contact clip 1 is depicted in FIG. 1.

The first terminal 3 comprises two tongues 7 with a slotted 8 located there between. The slot 8 extends in the longitudinal direction parallel to the longitudinal axis I. The tongues 7 have curved outer sides in the embodiment of FIGS. 1 to 3, thereby defining a portion of increased lateral extension. The tongues 7 may be elastically deformed by a narrowing slot 8, i.e. in a first direction D1 which is perpendicular to the longitudinal axis I.

The second terminal 4 is bent with respect to the plane of the substrate 2 by approximately 315° in the embodiment depicted in FIG. 2. The free edge of the second terminal 4 may be chamfered as depicted in the Figures. In the embodiment shown in FIGS. 1 to 3 the second terminal 4 is divided into three tongues. However, the second terminal 4 may alternatively be formed as a single element. The second terminal 4 is elastically deformable with respect to the substrate 2 in a second direction D2 which is perpendicular to the first direction D1 and perpendicular to the longitudinal axis I.

FIG. 4 depicts the contact clip 1 inserted into a chassis 9 which is only partially shown. The chassis 9 comprises several male plugs 10 which have the form of a slotted round pipe protruding from a surface of the chassis 9. This surface of the chassis 9 defines a first area for attachment of a PCB, whereas the opposite side or surface of the chassis 9 defines a second area for receiving further electronic components. The contact clips 1 are inserted into the slotted male plugs 10 such that the first terminal 3 is received in the respective slot 11 such that the portion of the first terminal 3 with the maximum lateral extension laterally protrudes through the slots 11 of the male plug 10.

As shown in FIG. 4, the thickness of the tongues 7 is slightly smaller than the width of the respective slot 11 such that the first terminal 3 is guided in the male plug 10 with a clearance fit.

The male plugs 10 each have a central longitudinal axis II which is, for example, perpendicular to the surface of the chassis 9 which forms the first PCB receiving area. The slot 11 of the respective male plug 10 extends in a plane defined by the central longitudinal axis II of the male plug 10 and a further axis III which is perpendicular to the central longitudinal axis II. The orientation of the further axis III is such that the male plug 10 is divided into two half-shells.

FIG. 5 shows the whole chassis 9 in a side view with portions of the first area having the male plugs 10 as enlarged details. In the depicted embodiment, the chassis 9 is a battery holder having in the second area, which is on the opposite side of the first area, a first compartment 12 for receiving an energy source, like a, preferably rechargeable, battery. Further, the chassis 9 comprises in the second area a second compartment 13 for receiving motor. The first compartment 12 may be provided with elastically deformable sidewalls 14 which are designed to receive and attach an energy source for example by means of clamping. The second compartment 13 may be provided with an end wall 15 for attachment of the motor.

In the embodiment of FIG. 5, the chassis 9 is provided with six slotted male plugs 10 which are each designed to receive a first terminal 3 of a respective contact clip 1 (not shown in FIG. 5). As shown in FIG. 5, the orientation of the slots 11 of the male plugs 10 may vary. As an alternative, the slots 11 may all have the same orientation.

In the embodiment of FIG. 5, two slotted male plugs 10a (located at the lower end as seen in FIG. 5) are designed and located to receive respective contact clips 1 which may be (directly or indirectly) connected to an external energy source, for example a recharging device. Two further slotted male plugs 10b are assigned to the first compartment 12 for receiving respective contact clips 1 which may be connected to an energy source. In addition, two slotted male plugs 10c are assigned to the second compartment 13 for receiving respective contact clips 1 which may be connected to an electrically driven motor. While the design depicted in FIG. 5 may be suitable for example for an electric shaver or an electric toothbrush, the location of the male plugs 10 and the arrangement of the compartments 12, 13 may vary for different types of devices.

Although not as depicted in FIGS. 4 and 5, the chassis 9 may further comprise one or more pins extending parallel to the male plugs 10. Such a pin may serve to align a PCB on the chassis 9. In addition, or as an alternative, the male plugs 10 may contribute in aligning a PCB on the chassis 9.

Figure 6:
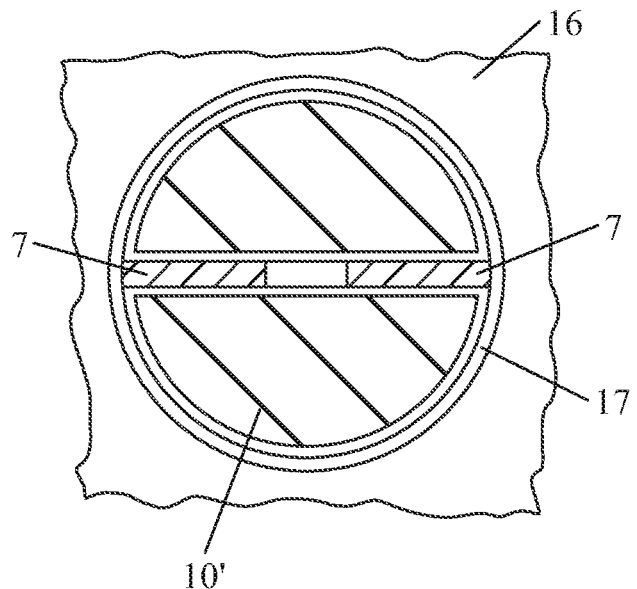
FIG. 6 shows a sectional view of a connector according to a second embodiment.
Figure 7:
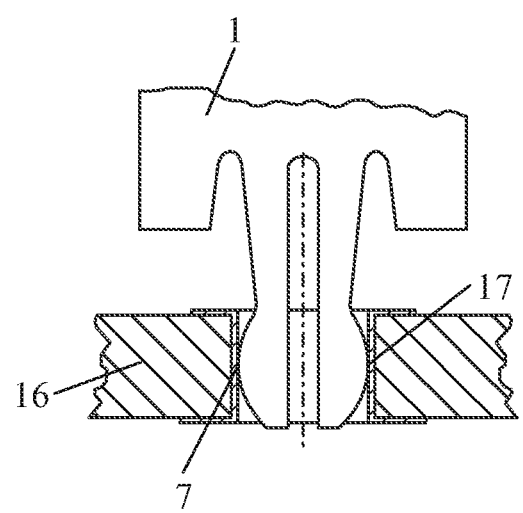
FIG. 7 shows a sectional view of a PCB with a connector according to a further embodiment.

FIGS. 6 and 7 show a PCB 16 with a via or plated-through opening 17, i.e. a bore or the like opening having an electrically conductive coating at least at its inner surface, and a male plug 10' (not shown in FIG. 7) with a contact clip 1 being received in the opening 17. The design of the male plug 10' differs from the design of the male plugs depicted in FIGS. 4 and 5 in that the slotted male plugs 10' rather have the form of a slotted cylinder than a slotted round pipe.

While FIG. 6 depicts the via or plated-through opening 17 in a substantially circular form, one or more of the various openings 17 in the PCB 16 may have a different form. For example, at least one of the vias or plated-through openings 17 may be designed as a long hole, thereby compensating tolerances of the chassis 9 and/or the PCB 16 when attaching the PCB 16 onto the chassis 9. Preferably, the orientation of such a long hole is such that the area of the inner surface of the long hole intended for contact with the tongues 7 of the contact pin 1 has an at least substantially constant width to permit reliable contact of the tongues 7 in the via or plated-through opening 17.

As can be seen in FIGS. 6 and 7, the first terminal 3 of contact clip 1 is received in the slot 11 of the male plug 10' with a clearance fit. Further, the male plug 10' is received in opening 17 with a clearance fit. In contrast to that, the rounded portion of the first terminal 3, i.e. the portion of the first terminal 3 with the largest width, is biased by the elastic deformation of the flexible tongues 7 to laterally protrude from slot 11 such that both tongues 7 are in contact with the plated-through opening 17, thereby establishing an electrically conductive connection between the contact clip 1 and the plated-through opening 17 of the PCB 16.

Figure 8:
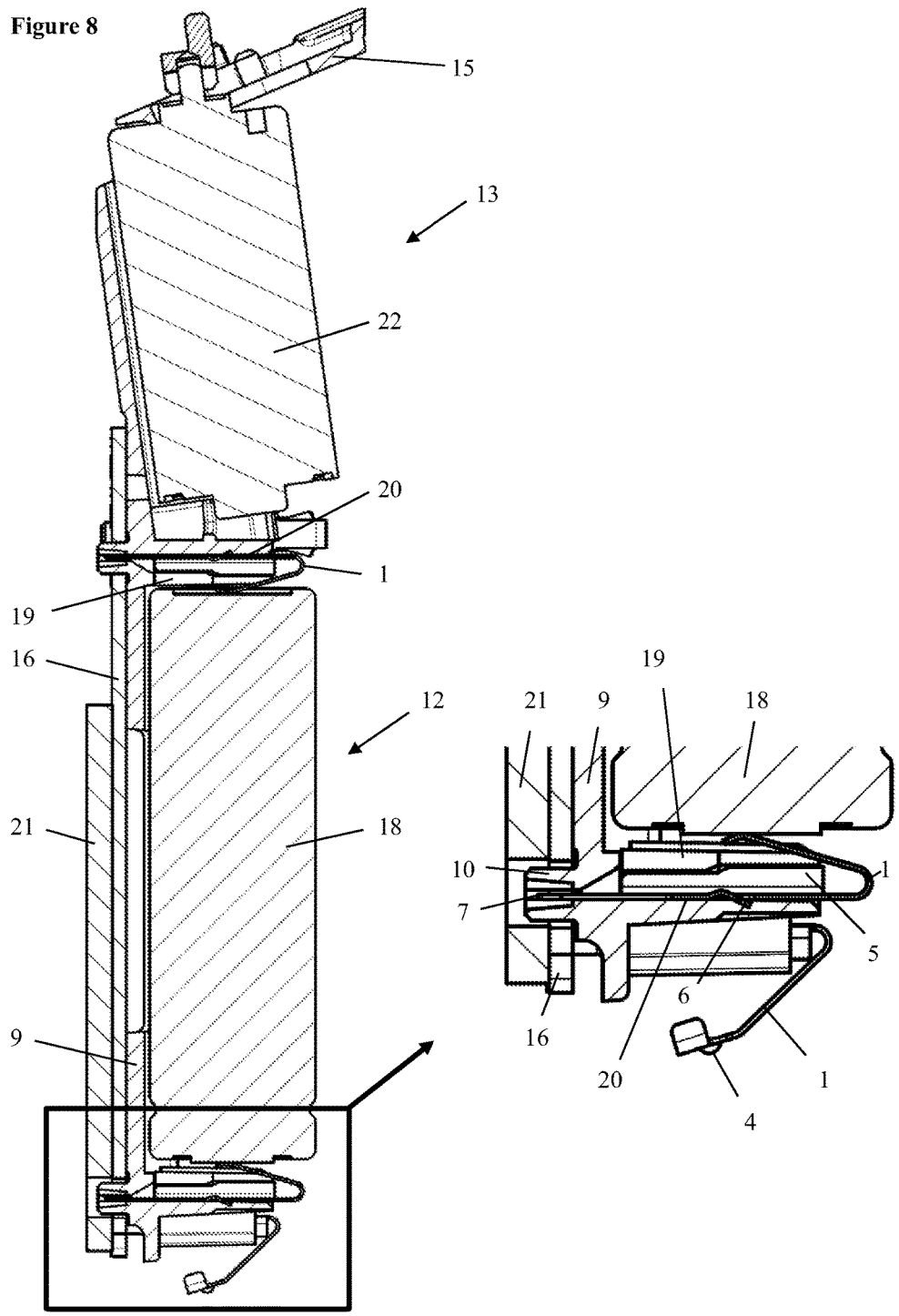
FIG. 8 shows a sectional view of a device with a connector according to a further embodiment with enlarged details.

FIG. 8 shows the chassis 9 with three contact clips 1 and the PCB 16 releasably attached to the chassis 9. In addition, an energy source 18 is depicted with the second terminals 4 of two opposed contact clips 1 being elastically deformed, thereby being biased against the energy source 18. In other words, the contact clips 1 are held in electrically conductive connection with the energy source 18 in a reliable manner due to the elastic bias of the second terminals 4. An electrically conductive connection between respective contact clips 1 and a motor 22 or the like electronic component and/or further terminals may be established in a similar manner. The contact clip 1 at the lower end of FIG. 8 is depicted in an unstressed condition, i.e. without the second terminal 4 being biased against a further component part.

FIG. 8 further shows how the substrate 2 of the contact clip 1 is guided and received in a respective portion of the chassis 9. In the example depicted in FIG. 8, a guiding channel 19 is formed in the chassis 9 receiving the substrate 2 and the optional guiding ribs 5 of the contact clip 1. The tongues 7 of the first terminal 3 extend through the respective slot 11 of the male plug 10 of the chassis 9. The second terminal 4 extends into the first compartment 12 such that the second terminal for may be bent (deflected) with respect to the substrate 2 and with respect to the chassis 9.

In the embodiment depicted in FIG. 8, the guiding channel 19 of the chassis 9 comprises a flat wall 20 against which the substrate 2 abuts. When inserting the contact clip 1 into the guiding channel 19, lug 6 is elastically deflected from the position depicted in FIG. 2 such that the contact clip 1 is firmly held in the guiding channel 19. The orientation of the lug 6 is such that movement of the contact clip 1 to the right as seen in FIG. 8, i.e. removal of the contact clip 1 from the guiding channel 19, is impeded. In this respect, the lug 6 may dig into wall 20 of the chassis 9, thereby holding the contact clip 1 firmly in the guiding channel 19. The design of the flat wall 20 in combination with the design and orientation of the lug 6 has the benefit that the more complex design of a latch attachment is not required for securing of the contact clip 1 in the guiding channel 19.

The design of the male plugs 10, 10a, 10b, 10c, 10' as depicted in the various embodiments is such that a PCB 16 may be attached to the chassis 9 or battery holder in a manner permitting easy detachment of the PCB 16 without requiring tools and without damaging the PCB 16 and/or portions of the chassis 9. In other words, the PCB 16 is mainly held on the chassis 9 by the elastic bias of the tongues 7 of the respective contact clips 1 received in the respective plated-through openings 17 and, optionally, by means of one or more positioning pins. If such positioning pins are present, the pins preferably do not latch into the PCB 16 but rather align the PCB 16 on the chassis 9. Depending on the material of the contact clip 1 and the plated-through opening 17, the tongues 7 may dig into the respective plated-through opening 17.

In addition to the above-mentioned releasable attachment of the PCB 16 on the chassis 9, the PCB 16 may be further held on the chassis 9 by biasing the PCB 16 out the chassis 9 against each other when they are received in a device. For example, the PCB 16 may be provided with a foam material 21 or the like compressible element holding the PCB 16 in its position on the chassis 9 under of the bias of the foam material 21 if the chassis 9 and the PCB 16 are both received in a common casing or a housing of a device. In more detail, the device may comprise a guiding channel for receiving the chassis 9 in a predefined orientation and alignment with a wall or protrusion of the device clamping the PCB 16 via the foam material 21 towards the chassis 9.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A connector comprising at least one contact clip, the contact clip comprising:

an electrically conductive substrate having a longitudinal axis, at least one lateral guiding rib extending substantially perpendicular to the substrate, a first terminal located at a first end of the substrate, wherein the first terminal comprises at least two contact tongues between which a longitudinal slot is formed, which contact tongues are elastically deformable with respect to each other in a first direction which is substantially perpendicular to the longitudinal axis, and a second terminal located at a second end of the substrate, wherein in its unstressed condition, the second terminal is bent with respect to the substrate and the first terminal and is elastically deformable with respect to the substrate in a second direction which is substantially perpendicular to the first direction and substantially perpendicular to the longitudinal axis.

2. The connector according to claim 1, wherein the contact clip further comprises at least one elastically deformable lug which, in its unstressed condition, is bent with respect to the substrate.

3. The connector according to claim 1, wherein the substrate, the first terminal and the second terminal of the contact clip are a single-piece component part comprising copper or a copper alloy.

4. The connector according to claim 1, wherein the contact tongues of the first terminal have a thickness between about 0.1 mm and about 0.35 mm.

5. A connector comprising at least one contact clip and a chassis, wherein the at least one contact clip comprises:

an electrically conductive substrate having a longitudinal axis, a first terminal located at a first end of the substrate, wherein the first terminal comprises at least two contact tongues between which a longitudinal slot is formed, which contact tongues are elastically deformable with respect to each other in a first direction which is substantially perpendicular to the longitudinal axis, and a second terminal located at a second end of the substrate, wherein in its unstressed condition, the second terminal is bent with respect to the substrate and the first terminal and is elastically deformable with respect to the substrate in a second direction which is substantially perpendicular to the first direction and substantially perpendicular to the longitudinal axis, wherein the chassis comprises:

a first area adapted for attachment of a PCB, the first area comprising at least one slotted male plug, and a second area adapted for attachment of at least one electronic component, wherein the first terminal of the at least one contact clip is received in the slot of the at least one male plug.

6. The connector according to claim 5, wherein the at least one male plug has the form of a slotted cylinder or a slotted round pipe, wherein the slot formed in the male plug extends in a plane defined by a central longitudinal axis of the male plug and an axis substantially perpendicular to the central longitudinal axis.

7. The connector according to claim 5, wherein the slot formed in the male plug has a width which is equal to or larger than the thickness of the first terminal of the at least one contact clip.

8. The connector according to claim 5, wherein the chassis further comprises a guiding channel receiving the substrate and the at least one lateral guiding rib of the at least one contact clip.

9. The connector according to claim 5, wherein the first area further comprises at least one positioning pin extending parallel to the at least one slotted male plug.

10. The connector according to claim 5, wherein the second area comprises a compartment for receiving an electric motor and a compartment for receiving an energy storage.

11. The connector according to claim 5, wherein the first area comprises six slotted male plugs, each receiving the first terminal of a respective one of the at least one contact clips, and that the second area comprises:
- a first compartment for receiving an electric motor, with the second terminals of two contact clips extending in the first compartment, and
- a second compartment for receiving an energy storage, with the second terminals of another two contact clips extending in the second compartment,
- wherein the second terminals of two further contact clips are positioned at a lateral side of the chassis.

12. The connector according to claim 5, further comprising a PCB releasably attached to the first area of the chassis, wherein the PCB comprises at least one plated-through opening receiving one of the at least one slotted male plugs of the chassis and the contact tongues of the first terminal of one of the at least one contact clips.

13. The connector according to claim 12, wherein the plated-through opening has a diameter in the direction of the slot of the one male plug which is smaller than the maximum width of the first terminal received in the respective plated-through opening.

14. The connector according to claim 12, wherein the plated-through opening has a diameter in the direction substantially perpendicular to the slot of the one male plug which is smaller than the maximum width of the one male plug received in the respective plated-through opening.

15. A body treatment device comprising an energy consumer, an electrical energy source, a PCB and at least one connector according to claim 1.

16. Assembly method for a connector comprising the steps of:
providing a chassis, an at least one contact clip and a PCB, wherein the at least one contact clip comprises:
- an electrically conductive substrate having a longitudinal axis,
- a first terminal located at a first end of the substrate, wherein the first terminal comprises at least two contact tongues between which a longitudinal slot is formed, which contact tongues are elastically deformable with respect to each other in a first direction which is substantially perpendicular to the longitudinal axis, and
- a second terminal located at a second end of the substrate, wherein in its unstressed condition, the second terminal is bent with respect to the substrate and the first terminal and is elastically deformable with respect to the substrate in a second direction which is substantially perpendicular to the first direction and substantially perpendicular to the longitudinal axis,
wherein the chassis comprises:
- a first area adapted for attachment of a PCB, the first area comprising at least one slotted male plug, and
- a second area adapted for attachment of at least one electronic component,
preassembling the chassis and the at least one contact clip by inserting the first terminal of the at least one contact clip into a slot of the at least one male plug of the chassis such that the at least two contact tongues of the first terminal laterally protrude from the at least one male plug in a first direction, and
releasably attaching the PCB on a first area of the chassis by inserting at least one slotted male plug into a plated-through opening of the PCB, wherein an elastic clamping force is generated between the PCB and the at least one contact clip by elastic deformation of the at least two contact tongues of the first terminal in the first direction.

17. The assembly method of claim 16, further comprising inserting the chassis, the at least one contact clip and the PCB into a housing so as to be fitted therein such that non release of the PCB from the chassis is secured.

* * * * *